US008037761B2

(12) United States Patent
Goto et al.

(10) Patent No.: US 8,037,761 B2
(45) Date of Patent: Oct. 18, 2011

(54) QUANTITATIVE EVALUATION DEVICE AND METHOD OF ATOMIC VACANCY EXISTING IN SILICON WAFER

(75) Inventors: Terutaka Goto, Niigata (JP); Yuichi Nemoto, Niigata (JP); Hiroshi Kaneta, Niigata (JP); Masataka Hourai, Tokyo (JP)

(73) Assignees: Niigata University, Niigata (JP); Sumco Corporation, Toyko (JP)

( * ) Notice: Subject to any disclaimer, the term of this patent is extended or adjusted under 35 U.S.C. 154(b) by 330 days.

(21) Appl. No.: 12/281,623

(22) PCT Filed: Mar. 2, 2007

(86) PCT No.: PCT/JP2007/054615
§ 371 (c)(1),
(2), (4) Date: Oct. 31, 2008

(87) PCT Pub. No.: WO2007/100155
PCT Pub. Date: Sep. 7, 2007

(65) Prior Publication Data
US 2009/0064786 A1    Mar. 12, 2009

(30) Foreign Application Priority Data
Mar. 3, 2006  (JP) ................................. 2006-058560

(51) Int. Cl.
*G01N 29/07* (2006.01)

(52) U.S. Cl. ................................ 73/597; 73/606; 73/632
(58) Field of Classification Search .................... 73/597, 73/632, 606; 438/14
See application file for complete search history.

(56) References Cited

U.S. PATENT DOCUMENTS
3,350,942 A * 11/1967 Peltola .......................... 374/119
(Continued)

FOREIGN PATENT DOCUMENTS
JP     1-98960 A     4/1989
(Continued)

OTHER PUBLICATIONS

International Search Report dated Apr. 24, 2007 for International Application No. PCT/JP2007/054615.

(Continued)

*Primary Examiner* — J M Saint Surin
(74) *Attorney, Agent, or Firm* — Sughrue Mion, PLLC

(57) ABSTRACT

There is provided a quantitative evaluation device or the like of atomic vacancy existing in a silicon wafer in which the atomic vacancy concentration in the silicon wafer can be quantitatively evaluated by forming a rationalized thin-film transducer on a surface of a silicon sample without conducting an acceleration treatment for enhancing the concentration. This is characterized by comprising a magnetic force generating means 2 for applying an external magnetic field to a silicon sample 5 cut out from a given site of a silicon wafer, a temperature controlling means 3 capable of cooling the silicon sample 5 to a temperature region of not higher than 50 K, a ultrasonic oscillating-detecting means 4 for oscillating ultrasonic pulse to the surface of the silicon sample 5 and propagating the oscillated ultrasonic pulse into the silicon sample 5 and detecting a change of sound velocity in the propagated ultrasonic pulse, wherein a thin-film transducer 8 having properties capable of following to an expansion of the silicon sample 5 at the above temperature region and substantially aligning C-axis in a given direction is directly formed on the surface of the silicon sample 5.

19 Claims, 15 Drawing Sheets

U.S. PATENT DOCUMENTS

| | | | |
|---|---|---|---|
| 6,221,743 B1 * | 4/2001 | Fujikawa et al. | 438/530 |
| 6,532,977 B2 * | 3/2003 | Otsuki et al. | 134/184 |
| 6,849,901 B2 * | 2/2005 | Falster | 257/347 |
| 6,930,375 B2 * | 8/2005 | Falster et al. | 257/618 |
| 7,048,824 B1 * | 5/2006 | Werfel et al. | 156/345.11 |
| 2009/0217866 A1 * | 9/2009 | Goto et al. | 117/15 |
| 2010/0111802 A1 * | 5/2010 | Umeno et al. | 423/325 |
| 2010/0186512 A1 * | 7/2010 | Goto et al. | 73/632 |

FOREIGN PATENT DOCUMENTS

| | | |
|---|---|---|
| JP | 7-174742 A | 7/1995 |
| JP | 3357227 B2 | 10/2002 |
| JP | 2005-37153 A | 2/2005 |

OTHER PUBLICATIONS

R. N. Kleiman et al., "Two-Level Systems Observed in the Mechanical Properties of Single-Crystal Silicon at Low Temperatures", Physical Review Letters, vol. 59, No. 18, 1987, p. 2079-2082.

T. Goto et al., "Observation of Low-Temperature Elastic Softening due to Vacancy in Crystalline Silicon", Journal of the Physical Society of Japan, vol. 75, No. 4, 2006, p. 044602.1-044602.6.

* cited by examiner

FIG. 10
Pulse width 0.2μs
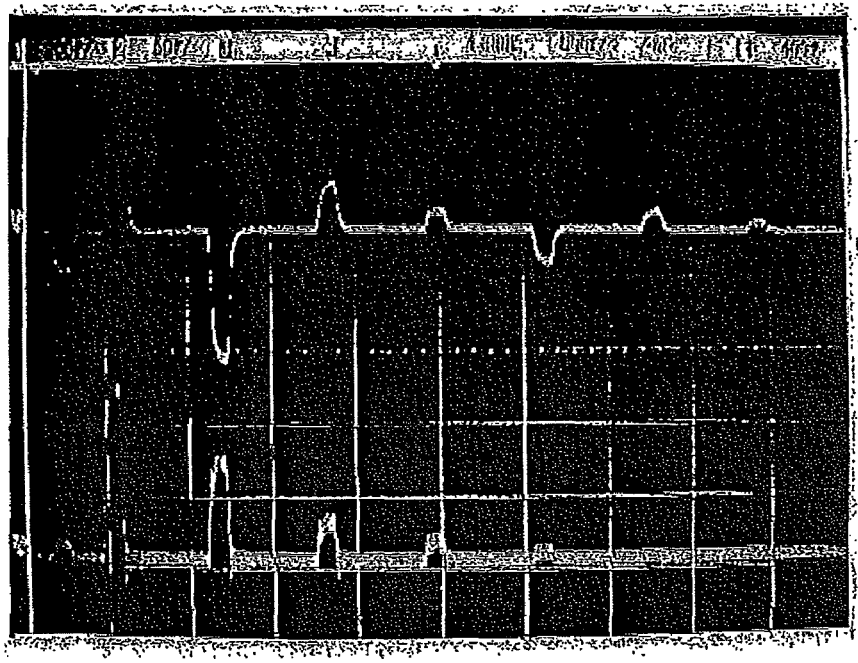
Pulse width 12μs

QUANTITATIVE EVALUATION DEVICE AND METHOD OF ATOMIC VACANCY EXISTING IN SILICON WAFER

TECHNICAL FIELD

This invention relates to a device and a method for quantitatively evaluating atomic vacancy existing in a silicon wafer which are capable of specifying kinds of atomic vacancies existing in a wafer of silicon crystal produced by a Czochralski method (CZ method) or a floating zone method (FZ method) used in a semiconductor industry and directly quantitatively evaluating an atomic vacancy concentration without estimating by a indirect method such as measurement of total void volume or the like.

RELATED ART

A silicon crystal is considered to be a most pure and ideal crystal got by human. However, entropy of free energy is existent in the crystal, so that the crystal disorder due to intrinsic point defects (atomic vacancy and interstitial silicon) is always existent in the crystal at a melting point of 1412° C. growing the crystal.

Heretofore, there is no means for measuring a quantity of isolated atomic vacancies existing in the silicon crystal. However, the existence of the atomic vacancy is qualitatively judged, for example, by conducting a heat treatment in the growing stage of silicon crystal or the heating stage in the production of silicon device to develop oxygen precipitates formed by the reaction between interstitial oxygen atom excessively existing in CZ crystal and the atomic vacancy. Also, the concentration of atomic vacancy introduced during the crystal growth is estimated by aggregating excessive atomic vacancies introduced during the solidification of the crystal at a cooling stage in the crystal growth to form voids having a size of about 100 nm as a secondary defect and then measuring a total volume of such voids through an infrared tomography. However, the latter method merely and indirectly measures the existing quantity of the atomic vacancies.

For this end, one of the inventors proposes a method wherein the concentration of atomic vacancies in the wafer of silicon crystal can be measured quantitatively without conducting an accelerated treatment in Patent Document 1. According to the method described in Patent Document 1, the concentration of intrinsic point defect can be determined based on a steep dropping quantity of a curve indicating a relationship between a change in ultrasonic velocity or a change in ultrasonic absorption of a crystal sample and a cooling temperature of the crystal sample by applying an exterior magnetic field to the crystal sample and passing ultrasonic wave through the crystal sample while cooling. Also, in order to conduct oscillation and receiving of ultrasonic pulse on a silicon wafer as a test material, a transducer made of, for example, $LiNbO_3$ is attached onto the surface of the silicon wafer through an adhesive.

Patent Document 1: JP-A-H07-174742

As a result of the inventors' further detailed examinations, however, when the silicon wafer is cooled to a cryogenic temperature of not higher than 50 K, the transducer may be partly peeled off from the surface of the silicon wafer due to the cooling, and there is caused a problem that if the transducer is peeled, the change in the ultrasonic pulse velocity propagating in the silicon sample can not be detected precisely.

The reason why the transducer is peeled off from the surface of the silicon wafer is considered due to the fact that when the sample is mainly cooled to the cryogenic temperature of not higher than 50 K, the transducer us shrunk, while the silicon wafer is expanded and hence a large difference in thermal expansion between the transducer and the silicon wafer is caused to produce the peeling.

DISCLOSURE OF THE INVENTION

Problems to be Solved by the Invention

It is, therefore, an object of the invention to provide a device and a method for quantitatively evaluating atomic vacancy existing in a silicon wafer in which a kind of atomic vacancy existing in the wafer of silicon crystal produced by the Czochralski method (CZ method) or the floating zone method (FZ method) used in the semiconductor industry can be specified by forming a rationalized thin-film transducer on a surface of a silicon sample and a concentration of atomic vacancy can be evaluated quantitatively without conducting an accelerated treatment for enhancing the concentration or the like.

Means for Solving Problems

In order to achieve the above object, the summary and construction of the invention are as follows.

(1) A device for quantitatively evaluating atomic vacancy existing in a silicon wafer, which comprises a magnetic force generating means for applying an external magnetic field to a silicon sample cut out from a given site of a silicon wafer, a temperature controlling means capable of cooling the silicon sample to a temperature region of not higher than 50 K, a ultrasonic oscillating-detecting means for oscillating ultrasonic pulse to the surface of the silicon sample and propagating the oscillated ultrasonic pulse into the silicon sample and detecting a change of sound velocity in the propagated ultrasonic pulse, wherein a thin-film transducer having properties capable of following to an expansion of the silicon sample associated with a temperature drop at the above temperature region and substantially aligning C-axis in a given direction is directly formed on the surface of the silicon sample.

(2) A device for quantitatively evaluating atomic vacancy existing in a silicon wafer according to the item (1), wherein the ultrasonic oscillating-detecting means comprises a means detecting a phase difference between a reference wave pulse signal directly measured on the oscillated ultrasonic pulse and a sample passing wave pulse signal measured after the ultrasonic pulse is propagated into the silicon sample.

(3) A device for quantitatively evaluating atomic vacancy existing in a silicon wafer according to the item (1) or (2), wherein the thin-film transducer is made from zinc oxide (ZnO) or aluminum nitride (AlN).

(4) A device for quantitatively evaluating atomic vacancy existing in a silicon wafer according to the item (1), (2) or (3), wherein the thin-film transducer is formed on the silicon wafer through a physical deposition method.

(5) A device for quantitatively evaluating atomic vacancy existing in a silicon wafer according to any one of the items (1)-(4), wherein a gold thin film is provided between the thin-film transducer and the silicon crystal.

(6) A device for quantitatively evaluating atomic vacancy existing in a silicon wafer according to any one of the items (1)-(5), wherein the thin-film transducer has a C-axis inclined at an angle of 5-60° with respect to the surface of the silicon sample, and measures at least a transverse wave component among vertical wave component and transverse wave component propagated and detected in the silicon sample.

(7) A device for quantitatively evaluating atomic vacancy existing in a silicon wafer according to any one of the items (1)-(6), wherein the thin-film transducer has a thickness of 0.5-200 μm.

(8) A device for quantitatively evaluating atomic vacancy existing in a silicon wafer according to any one of the items (1)-(7), wherein the thin-film transducer has a resonance frequency of 10 MHz-10 GHz.

(9) A device for quantitatively evaluating atomic vacancy existing in a silicon wafer according to any one of the items (1)-(8), wherein the magnetic force generating means is a range of 0-20 tesla.

(10) A device for quantitatively evaluating atomic vacancy existing in a silicon wafer according to any one of the items (1)-(9), wherein the temperature controlling means comprises a dilution refrigerator capable of cooling up to a cryogenic temperature of 5 mK.

(11) A device for quantitatively evaluating atomic vacancy existing in a silicon wafer according to any one of the items (1)-(10), wherein the ultrasonic oscillating-detecting means uses a ultrasonic pulse having a pulse width of not less than 10 μs.

(12) A device for quantitatively evaluating atomic vacancy existing in a silicon wafer according to any one of the items (1)-(11), wherein the ultrasonic oscillating-detecting means comprises a means for varying an oscillation frequency so as to render a phase difference produced by changing a sound velocity at a temperature or a magnetic field to conduct zero detection.

(13) A device for quantitatively evaluating atomic vacancy existing in a silicon wafer according to any one of the items (1)-(12), which is capable of simultaneously measuring phase difference at a plurality of silicon samples or at plural points of a single silicon sample to be measured.

(14) A method for quantitatively evaluating atomic vacancy existing in a silicon wafer, which comprises oscillating a ultrasonic pulse onto a silicon sample cut out from a given site of a silicon wafer and directly provided on its surface with a thin-film transducer having properties capable of following to expansion associated with a temperature drop of the silicon sample at a temperature region of not higher than 25 K at a state of applying an exterior magnetic field, if necessary, while cooling at the above temperature region; propagating the oscillated ultrasonic pulse into the silicon sample; detecting a change of sonic velocity in the propagated ultrasonic pulse; calculating a reducing quantity of elastic constant associated with the drop of the cooling temperature from the change of sonic velocity; and quantitatively evaluating a kind and a concentration of atomic vacancy existing in the silicon wafer from the calculated reducing quantity of elastic constant.

EFFECT OF THE INVENTION

According to the invention, the kind of atomic vacancy existing in the wafer of silicon crystal produced by the Czochralski method (CZ method) or the floating zone method (FZ method) used in the semiconductor industry can be specified by forming the rationalized thin-film transducer on the surface of the silicon sample, and the existing concentration of atomic vacancy can be directly evaluated quantitatively without conducting an accelerated treatment for enhancing the concentration or the like.

BRIEF DESCRIPTION OF THE DRAWINGS

FIG. 10 is a view showing an example of a pulse signal applied to a transducer, wherein an upper part is a case that a pulse width is 0.2 μs and a lower part is a case that a pulse width is 12 μs.

BEST MODE FOR CARRYING OUT THE INVENTION

Next, a device for quantitatively evaluating atomic vacancy existing in a silicon wafer according to the invention will be described with reference to the accompanying drawings.

Figure 1:
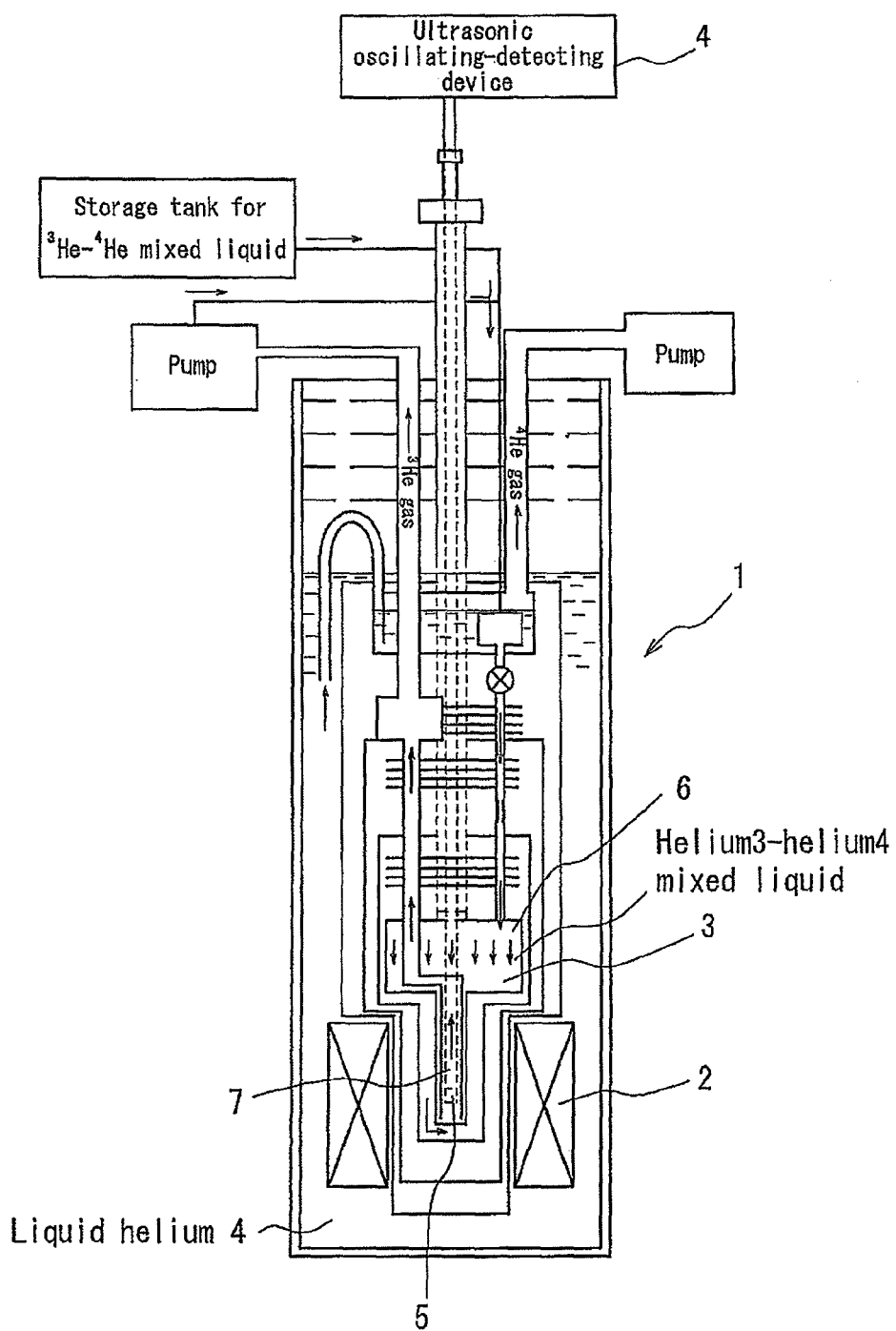
FIG. 1 is a schematic view of a device for quantitatively evaluating atomic vacancy according to the invention.

FIG. 1 is a schematic view of a device for quantitatively evaluating atomic vacancy according to the invention.

The illustrated quantitative evaluation device 1 is mainly constituted with a magnetic force generating means 2, a temperature control means 3 and a ultrasonic oscillating-detecting means 4.

The magnetic force generating means 2 is arranged around a setting position of a silicon sample 5 so as to apply an external magnetic field to the silicon sample 5 cut out from a given site of a silicon wafer. As the magnetic force generating means 2 is mentioned, for example, a superconducting magnet. Also, according to the invention, a change of sound velocity in a ultrasonic pulse propagated in the silicon sample 5 is detected at a state of applying an external magnetic field to the silicon sample 5, if necessary, so that it is preferable that the magnetic force generating means 2 is controllable within a range of 0-20 tesla, more particularly 0-6 tesla (see FIG. 9). For example, the kind of atomic vacancy isolated in the wafer of silicon crystal can be specified by applying the external magnetic field as mentioned later.

The temperature control means 3 is constituted so that the silicon sample 5 can be cooled and controlled to a temperature region of not higher than 50 K. In FIG. 1 is shown a case of using a dilution refrigerator as the temperature control means 3. For example, the dilution refrigerator can control the cooling to a cryogenic temperature of 4.2 K at an upper side of the device and 5 mK at a lower side of the device by properly circulating a mixed liquid of $^3$He and $^4$He in a mixing chamber 6. Moreover, FIG. 1 shows a construction that a sample holder part 7 setting the silicon sample 5 therein is directly cooled by immersing into the mixed liquid of $^3$He and $^4$He in the mixing chamber 6, but the invention is not limited to only such a construction. For example, a member forming the cooled mixing chamber 6 is made from a material having a high heat conductivity, in which the silicon sample 5 can be indirectly cooled by utilizing a heat conduction from the member forming the mixing chamber. The latter case is particularly advantageous in a point that the temperature region to be cooled is widened toward a higher temperature side.

The ultrasonic oscillating-detecting means 4 is arranged for oscillating ultrasonic pulse onto the surface of the silicon sample 5 and propagating the oscillated ultrasonic pulse into the silicon sample 5 and then detecting a change of sound velocity in the propagated ultrasonic pulse.

Figure 2:
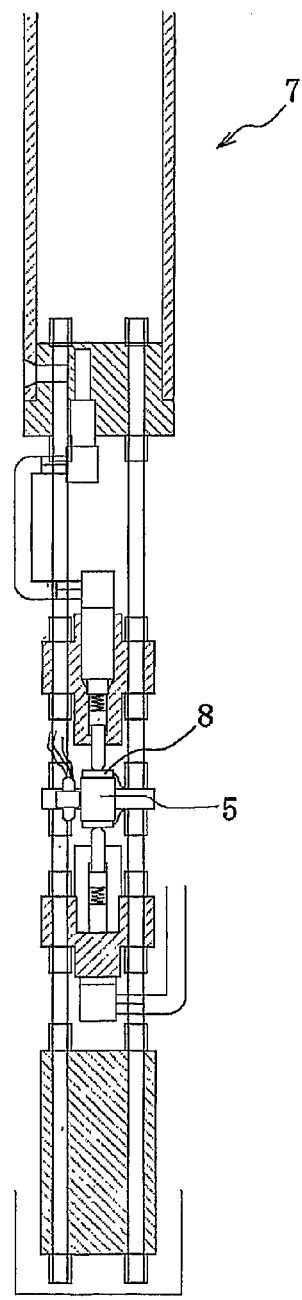
FIG. 2 is an enlarged view when a sample holder part 7 set with a silicon sample 5 is drawn out from a quantitative evaluation device 1.

FIG. 2 is an enlarged view of the sample holder part 7 set with the silicon sample 5 drawn out from the quantitative evaluation device 1 of FIG. 1.

In the invention, a thin-film transducer 8 having properties capable of following to the expansion of the silicon sample 5 at a temperature region of not higher than 50 K and having a C-axis aligned in a given direction is formed on the surface of the silicon sample 5 directly or indirectly through a metal thin film prior to the setting of the silicon sample 5. By adopting this construction, the thin-film transducer can be followed to the expansion of the silicon wafer even if the silicon wafer is cooled to a cryogenic temperature of not higher than 50 K, so that the peeling of the thin-film transducer is not caused by the aforementioned cooling and the change of sound velocity in the ultrasonic pulse propagated in the silicon sample can be detected precisely, and hence the kind and existing concentration of atomic vacancy isolated in the wafer of silicon crystal can be directly evaluated stable and quantitatively without conducting an accelerated treatment for enhancing the concentration, or the like.

Figure 3:
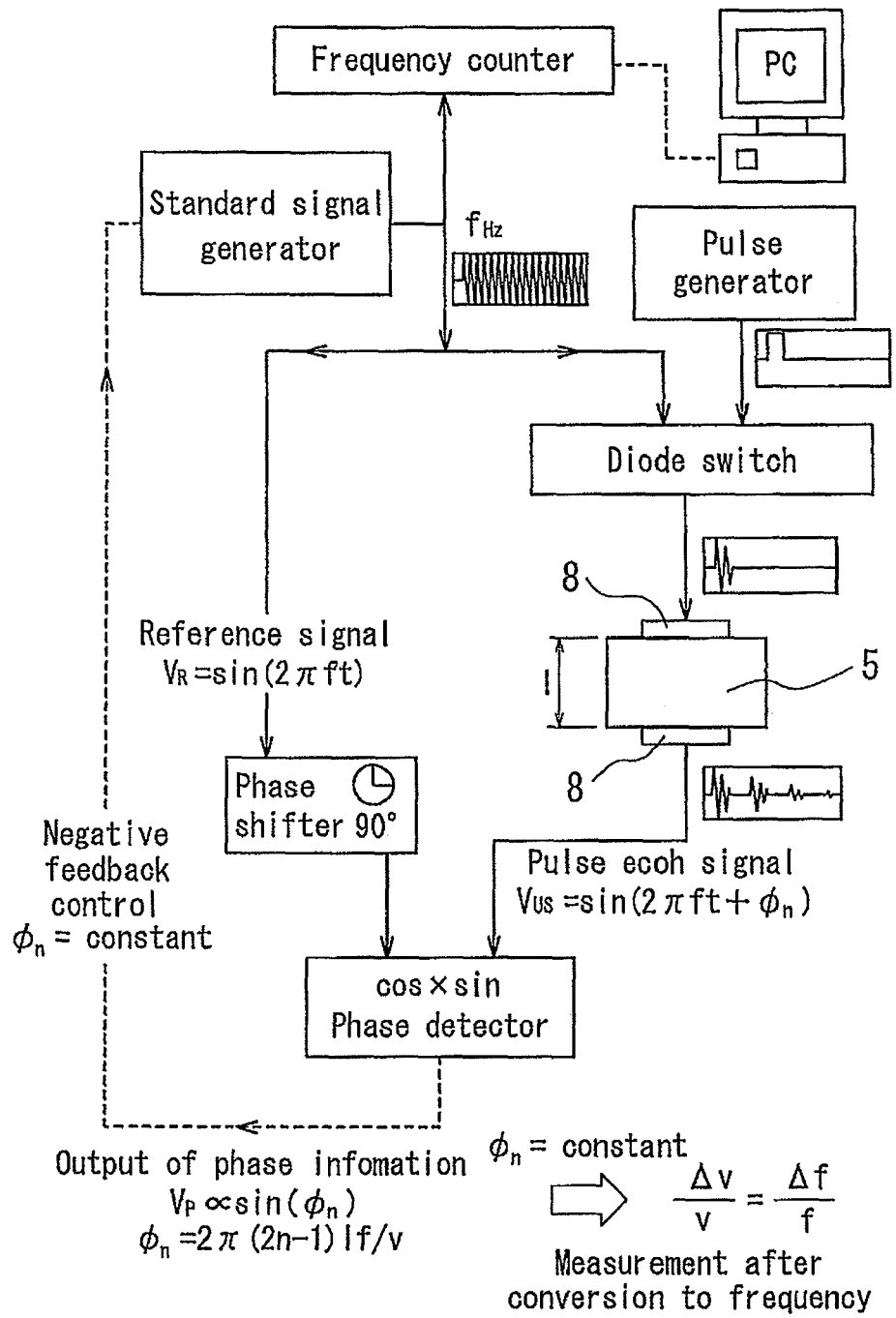
FIG. 3 is a flow chart explaining a method of detecting phase difference by using ultrasonic pulse.

Also, the ultrasonic oscillating-detecting means is preferable to be a means for detecting a phase difference between a reference wave pulse signal directly measuring the oscillated ultrasonic pulse and a sample passing wave pulse measured after the ultrasonic pulse is propagated into the silicon sample as shown in FIG. 3.

The thin-film transducer 8 is preferable to be made of zinc oxide (ZnO) or aluminum nitride (AlN).

It is preferable that the thin-film transducer 8 is formed on the silicon wafer by a physical deposition method such as sputtering in a point that zinc oxide (ZnO) or the like is densely bonded to the silicon wafer at an atomic level to form the zinc oxide (ZnO) having an excellent adhesiveness on the silicon wafer and hence the properties capable of following to the expansion of the silicon sample 5 at the temperature region of not higher than 50 K.

In addition, it is preferable to provide a gold deposited film between the thin-film transducer 8 and the silicon sample 5 in a point that the peeling during the cooling is prevented and the electric conduction is enhanced.

The thin-film transducer 8 is preferable to have a C-axis inclined at an angle of 5-60° with respect to the surface of the silicon sample in a point that at least a transverse wave component is measured among longitudinal wave component and transverse wave component in the ultrasonic wave propagated and detected in the silicon sample, whereby shear component is increased and the resolution is improved. When the angle is less than 5°, the longitudinal wave component included in the ultrasonic wave is substantially generated and the efficiency of generating the transverse wave component is considerably decreased, while when the angle exceeds 60°, both the efficiencies of generating the transverse ultrasonic wave and the longitudinal ultrasonic wave are considerably decreased.

Figure 14:
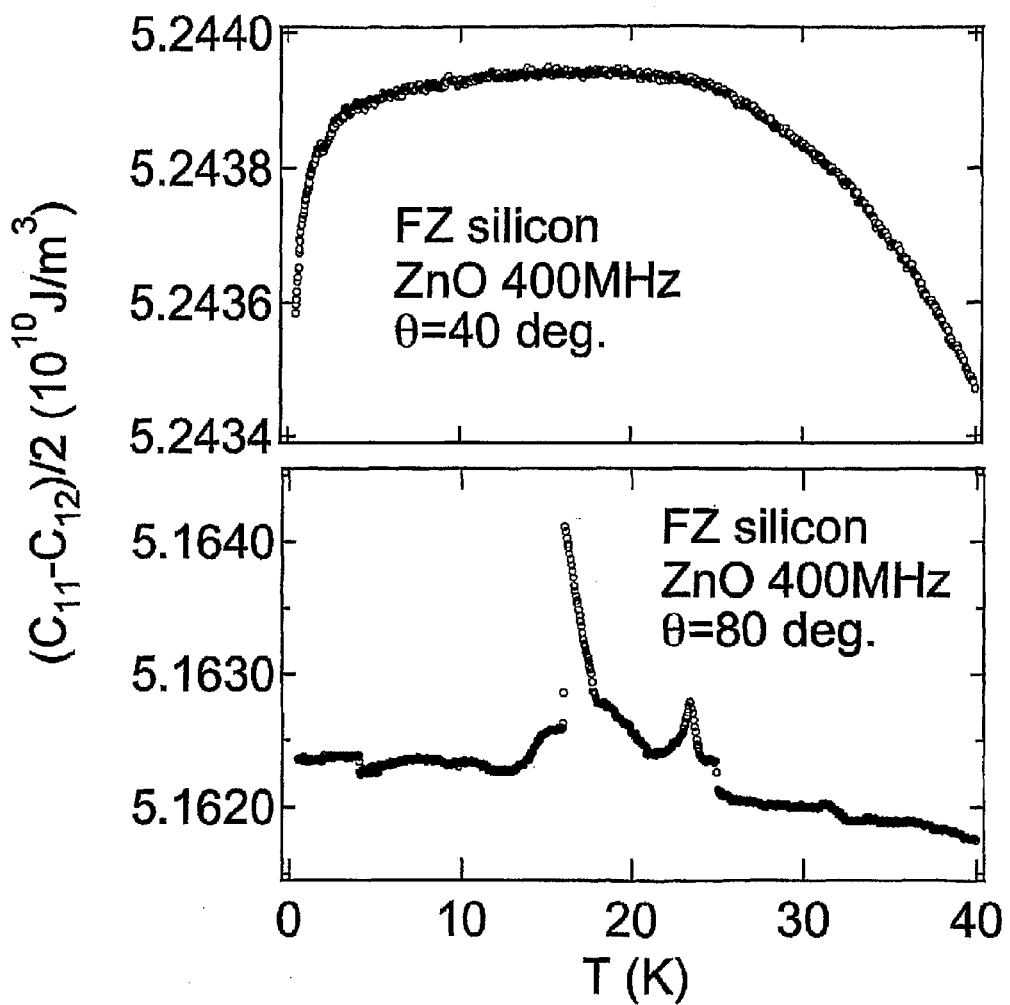
FIG. 14 is a graph showing results of ultrasonic measurement at a resonance frequency of 400 MHz on each of specimens obtained when ZnO is formed on two FZ silicon crystal wafers cut out from the same sample at a C-axis inclination angle of 40° or 80° with respect to the surface of the sample.

Moreover, the angle of the C-axis is more preferable to be a range of 40-50° in a point that both the efficiencies of generating the longitudinal ultrasonic wave and the transverse ultrasonic wave are enhanced well-balancedly. In FIG. 14 are shown results of ultrasonic measurement at a resonance frequency of 400 MHz on each of specimens obtained when ZnO as a transducer is formed on two FZ silicon crystal wafers cut out from the same sample at C-axis inclination angles of 40° and 80° with respect to the surface of the sample, respectively. From the results of FIG. 14, it is understood that when the C-axis angle is 40°, the change of elastic constant at the cryogenic temperature region can be measured precisely, whereas when the C-axis angle is 80°, the generations of the longitudinal ultrasonic wave and the transverse ultrasonic wave are small and hence the change of elastic constant at the cryogenic temperature region can not be measured.

As a method of preparing the thin-film transducer 8 having a C-axis inclined at a given angle is mentioned, for example, a method wherein the silicon sample is arranged obliquely with respect to a ZnO target.

The thin-film transducer 8 is preferable to have a thickness of 0.5-200 μm in a point that measurable ultrasonic waves can be generated. When the thickness exceeds 200 μm, there is a tendency of lowering the measuring precision, while when the thickness is less than 0.5 μm, it tends to make the electric measurement at a higher frequency difficult.

The resonance frequency of the thin-film transducer 8 is preferable to be a range of 10 MHz-10 GHz in a point that the ultrasonic measurement is applicable. When the resonance frequency is higher than 10 GHz, it tends to make the electric measurement at a higher frequency difficult, while when it is less than 10 MHz, there is a tendency of lowering the measuring precision.

In the ultrasonic oscillating-detecting means 4, it is preferable to use a ultrasonic pulse having a pulse width of not more than 10 μs in a point that it is possible to measure a sound velocity of a silicon sample having a thickness of not more than 10 mm. When the pulse width exceeds 10 μs, there is a tendency of making the distinction between the adjacent pulses difficult. In FIG. 10 are shown an upper part that the pulse width is 0.2 μs and a lower part that the pulse width is 12 μs.

The ultrasonic oscillating-detecting means 4 is more preferable to have a means for conducting zero detection by varying an oscillation frequency so as to make constant a phase difference produced due to the change of sound velocity through temperature or magnetic field.

Figure 11:
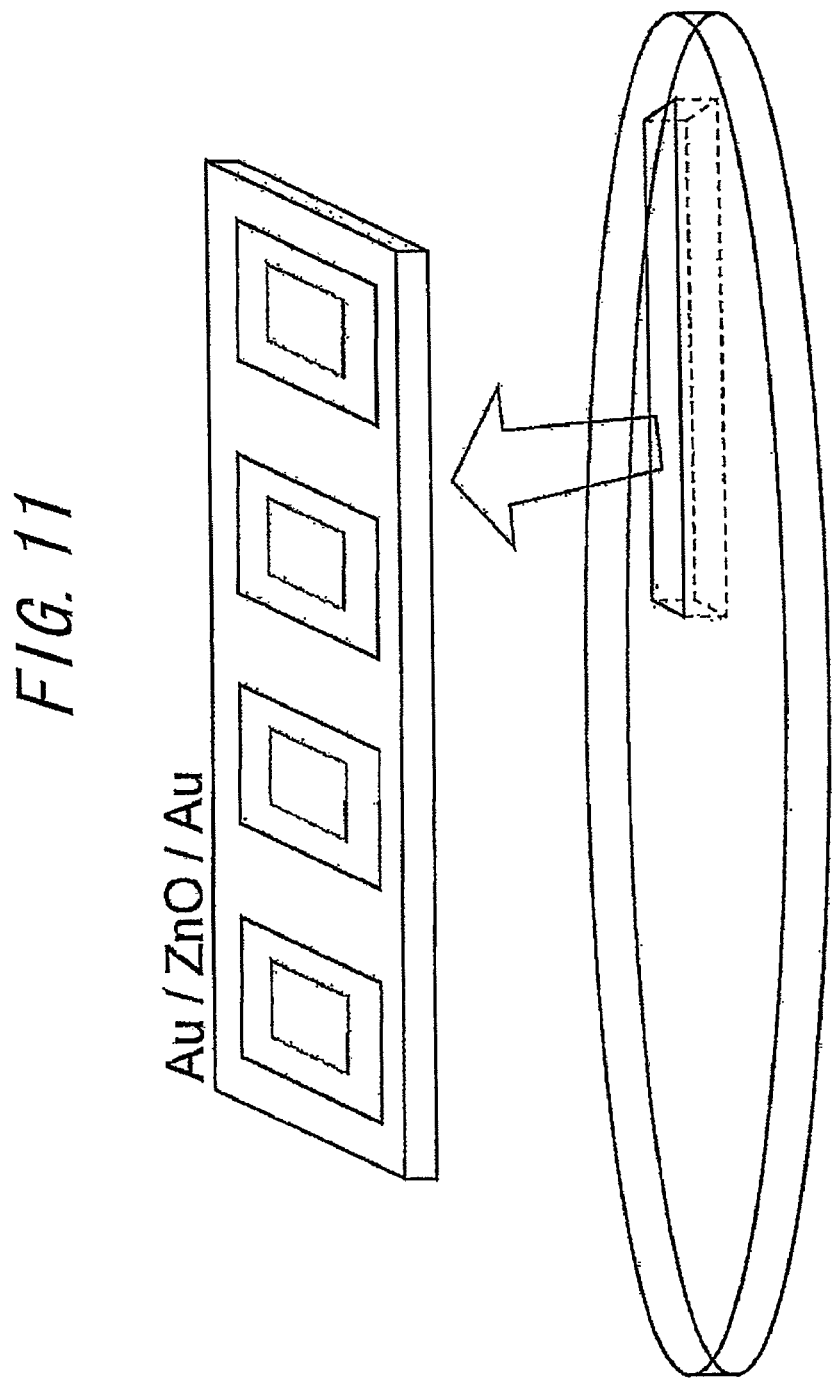
FIG. 11 is a schematic view illustrating an example that a transducer is directly formed on a silicon wafer by depositing gold (Au)/zinc oxide (ZnO)/gold (Au) on 4 places of the wafer for simultaneous phase measurement.

Also, it is preferable that the quantitative evaluation device 1 according to the invention can simultaneously measure phase differences with respect to a plurality of silicon samples and plural places of a single silicon sample. In FIG. 11 is shown an example that a transducer is directly formed on a single silicon wafer by depositing gold (Au)/zinc oxide (ZnO)/gold (Au) for simultaneously measuring phases at plural places of the wafer (4 places in FIG. 11).

Figure 4:
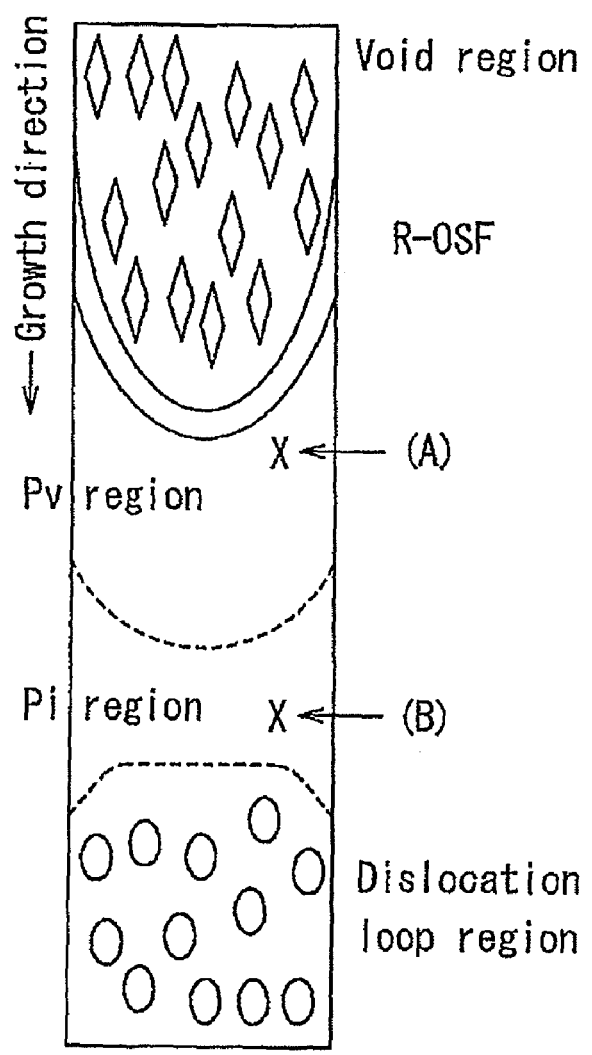
FIG. 4 is a schematically cross-sectional view illustrating an embodiment of a non-doped CZ silicon ingot.

FIG. 4 is a schematically cross-section view of a prototype non-doped CZ silicon ingot having a diameter of 6 inches. As seen from FIG. 4, it is confirmed that intrinsic point defect regions extending over about 3 cm (Pv region and Pi region) are existent in a central portion.

Figure 5:
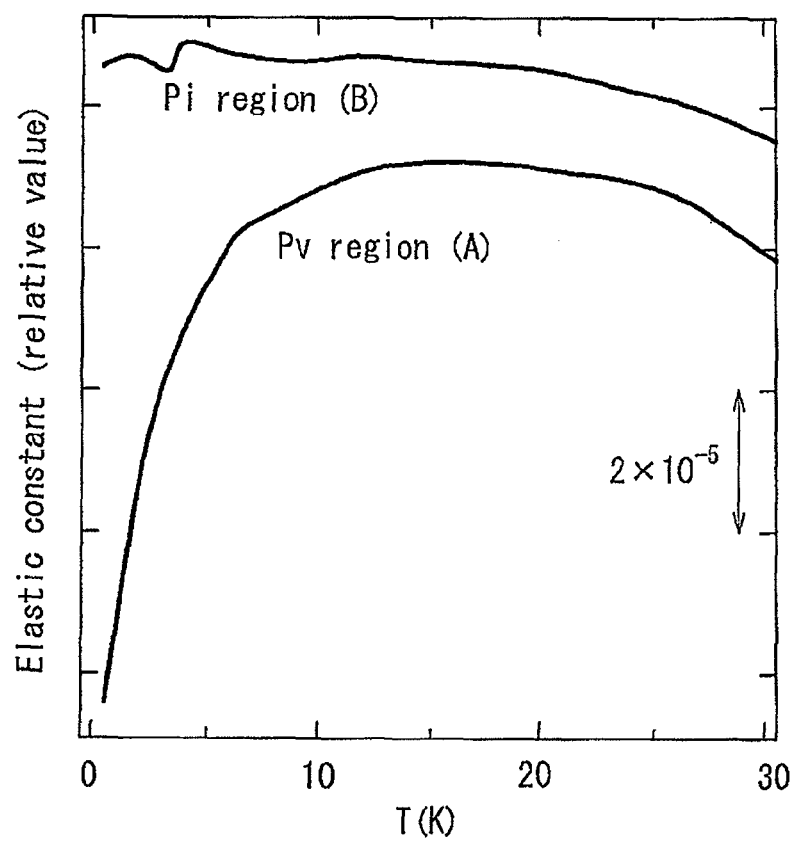
FIG. 5 is a graph showing a change of elastic constant on a cooling temperature measured according to the quantitative evaluation method of the invention when being cooled to 30 K-20 mK.

Then, silicon samples (A) and (B) having a size of 4 mm×4 mm×7 mm are cut out from the Pv region and Pi region as the intrinsic point defect region, respectively, and placed in the quantitative evaluation device shown in FIGS. 1 and 2, and then the change of elastic constant to cooling temperature is measured by the quantitative evaluation method according to the invention when they are cooled to 30 K-20 mK. The measured results are shown in FIG. 5. Moreover, a sound velocity v used in the measurement of elastic constant is calculated according to the following equation using a phase difference $\phi_n$ of ultrasonic pulse detected in FIG. 3:

$$\phi_n = 2\pi(2n-1)lf/v \qquad \text{Equation:}$$

wherein (2n−1)l is a propagation length of n-th echo and f is a ultrasonic frequency.

From the results of FIG. 5, it is understood that in the sample (A) of PV region in which a frozen atomic vacancy region was considered to be rich, the elastic constant considerably lowers in proportion to an inverse of a temperature at the cryogenic temperature region of 20 K-10 mK, and in other words, it is softened at a lower temperature. On the other hand, such a lowering of the elastic constant is not detected in the sample (B) of the Pi region in which silicon between lattices was considered to be rich.

Figure 15:
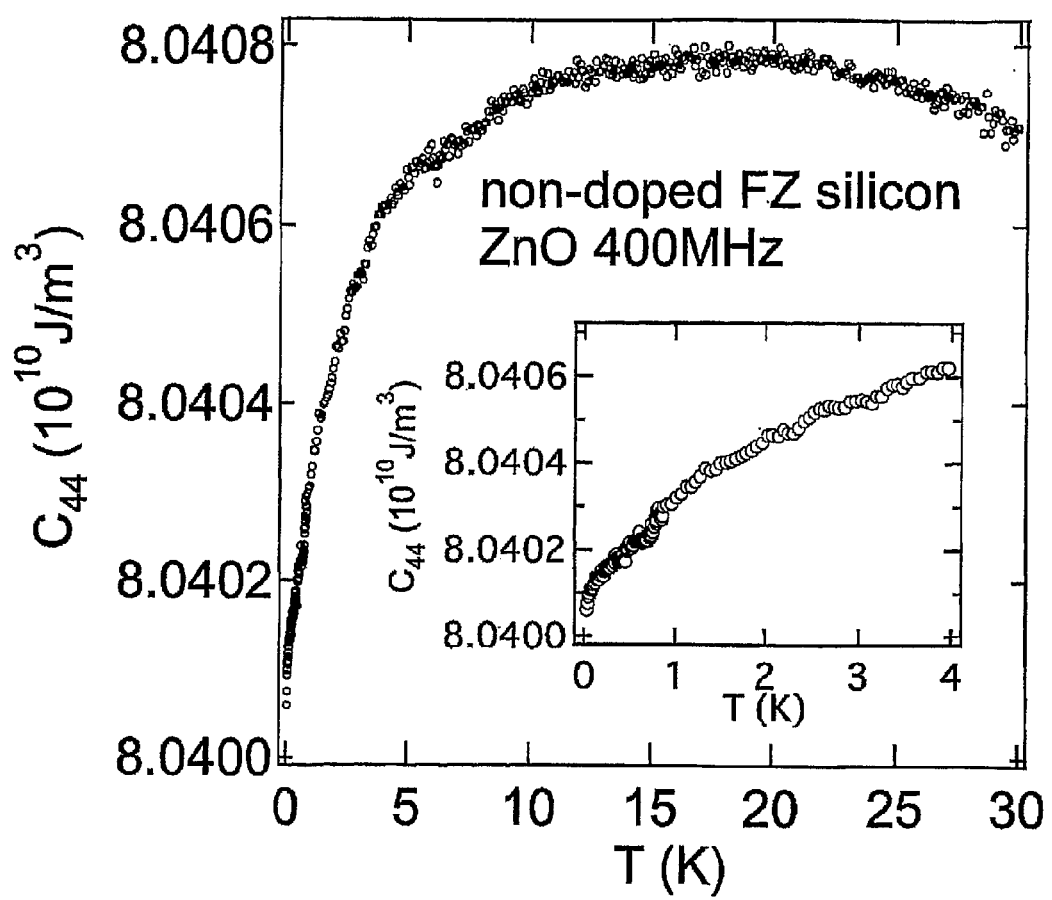
FIG. 15 is a graph showing results measured on a change of elastic constant to a temperature in a sample obtained by forming ZnO as a transducer on FZ silicon crystal.

Also, FIG. 15 shows an example of results measured on the change of elastic constant to a temperature with respect to a sample obtained by forming ZnO as a transducer on FZ silicon crystal. In FIG. 15, the measurement is conducted to a cryogenic temperature of 20 mK by using a dilution refrigerator as a temperature control means. From the results shown in FIG. 15, it is confirmed that the softening phenomenon at a lower temperature is detected even in the FZ silicon crystal likewise the above CZ silicon crystal.

Figure 9:
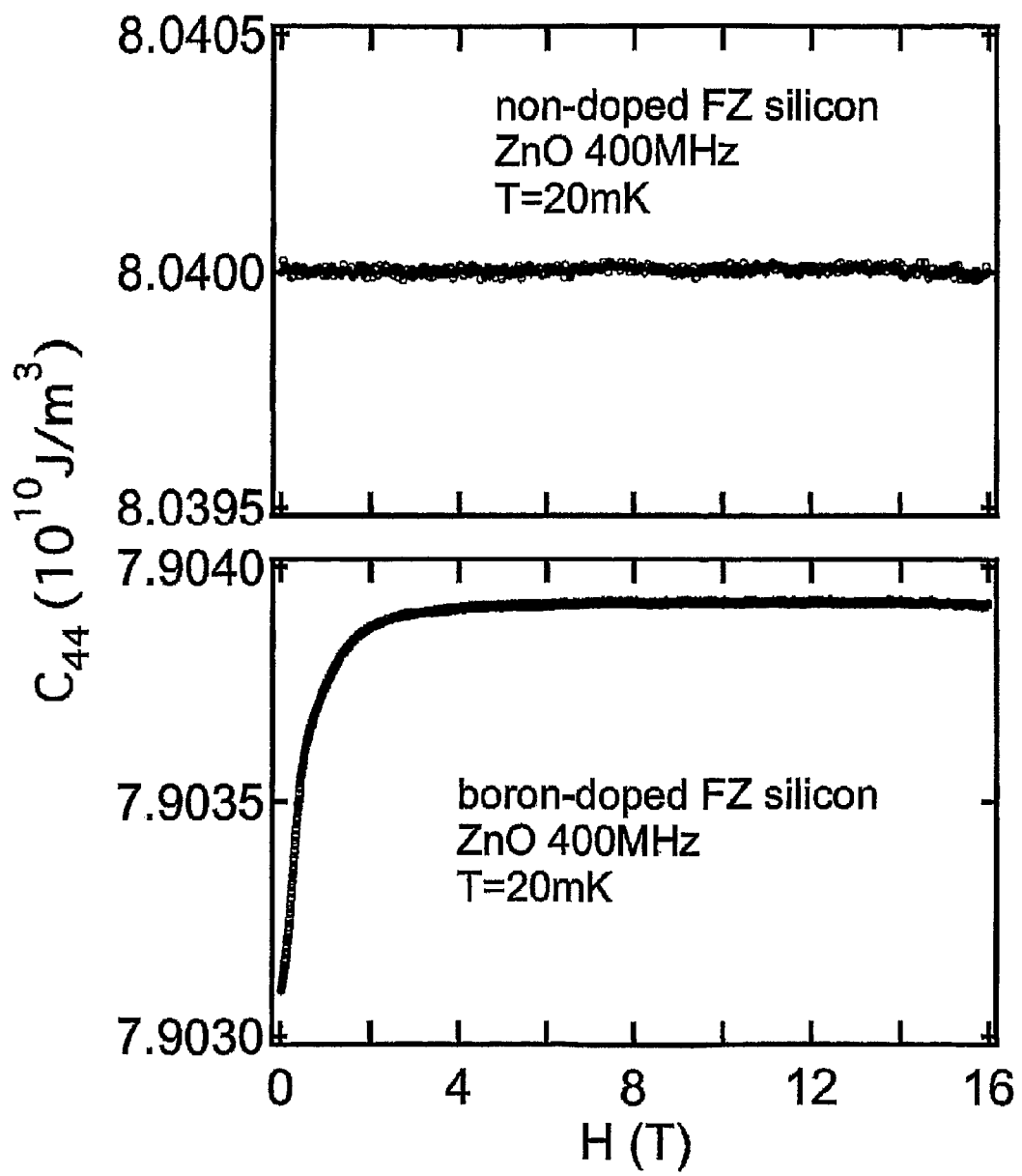
FIG. 9 is a graph showing an example of results on a change of elastic constant plotted by applying a magnetic field when using FZ silicon single crystal not added with B (upper part) and B-doped FZ silicon single crystal (lower part).

Further, magnetic filed dependency is investigated by using a B-doped FZ silicon single crystal and a FZ silicon single crystal not added with B, respectively. FIG. 9 shows an example of results on the change of elastic constant when applying a magnetic field of 0-16 tesla, wherein an upper part is a case of adding no B and a lower part is a case of adding B. From the results of FIG. 9, it is found out that the low-temperature softening phenomenon in the B-doped FZ silicon single crystal is caused by applying a magnetic field of not more than about 4 tesla but disappears in the application of a magnetic field exceeding the above value, whereas the low-temperature softening phenomenon in the non-doped FZ silicon single crystal is not caused over the whole range of the magnetic field. This shows that the bonding between charge state and strain in the atomic vacancy is an origin of the softening phenomenon. The atomic vacancy of the non-doped FZ silicon single crystal has a non-magnetic charge state trapped with 4 electrons, while that of the B-doped FZ silicon single crystal has a magnetized charge state trapped with 3 electrons. That is, it is considered that the molecular orbital of the atomic vacancy is disrupted into singlet and triplet and the Jahn-Teller effect through the bonding between electric quadrupole in the triplet and strain causes the low-temperature softening phenomenon of $C_{44}$ and $(C_{11}-C_{12})/2$. In the non-doped ZF silicon single crystal, it is seen that an antiferroquadrupolar interaction is existent among the atomic vacancies and hence $T_d$ symmetric property around the atomic vacancy is kept even at a minimum temperature of 20 mK to degenerate the triplet to thereby fluctuate the electric quadrupole.

From these results, it has been found that there is a magnetic field dependence in the low-temperature softening phenomenon of the elastic constant through the atomic vacancy wherein the number of trapped electrons is odd (3 or 5), while there is no magnetic field dependence in the low-temperature softening phenomenon of the elastic constant through the atomic vacancy wherein the number of trapped electrons is even (4). In the invention, therefore, the kind of the atomic vacancy can be determined from the presence or absence of the magnetic field dependence.

An example of the method for quantitatively evaluating atomic vacancy existing in the silicon wafer according to the invention will be explained below.

In the quantitative evaluation method according to the invention, the kind and concentration of atomic vacancy existing in the silicon wafer can be quantitatively evaluated by oscillating a ultrasonic pulse onto a silicon sample cut out from a given site of the silicon wafer and directly provided on its surface or indirectly provided through a gold thin film with a thin-film transducer having properties capable of following to expansion associated with a temperature drop of the silicon sample at a temperature region of not higher than 25 K at a state of applying an exterior magnetic field, if necessary, while cooling at the above temperature region; propagating the oscillated ultrasonic pulse into the silicon sample; detecting a change of sonic velocity in the propagated ultrasonic pulse; calculating a reducing quantity of elastic constant associated with the drop of the cooling temperature from the change of sonic velocity.

Although the above is merely described with respect to an embodiment of the invention, various modifications may be added in the claims.

EXAMPLES

A concentration of atomic vacancy existing in a silicon wafer is quantitatively evaluated by using the quantitative evaluation device of atomic vacancy existing in the silicon wafer according to the invention, which will be described below.

Example

Figure 6:
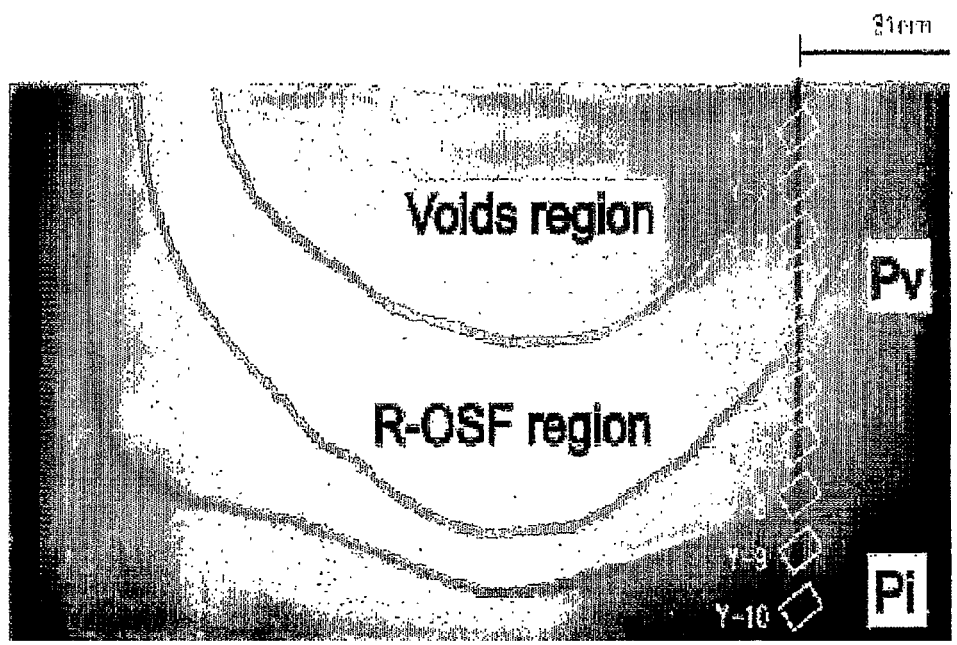
FIG. 6 is a cross-sectional view of a non-doped CZ silicon ingot used in an Example, wherein each existing region (void region, R-OSF region, $P_v$ region, $P_i$ region) is shown at a state of specifying a border line of the each region by using a Cu decoration method.
Figure 7:
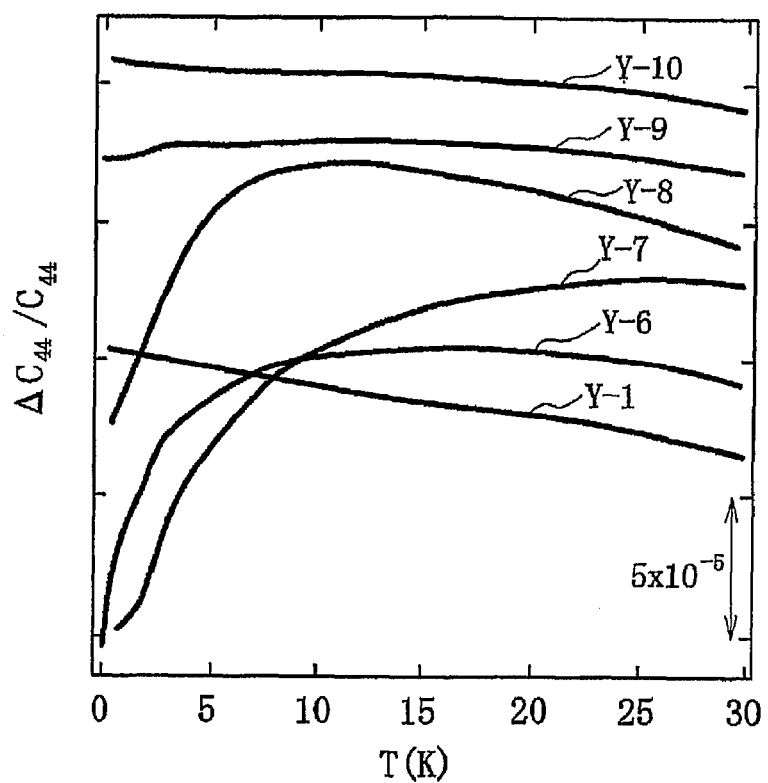
FIG. 7 is a graph showing a change of elastic constant on a cooling temperature ($\Delta C_{Z[111]}/C_{Z[111]}$) measured when samples (Y-1 and Y-6~Y-10) are cooled to 30 K-20 mK at 6 places shown in FIG. 6.

A non-doped CZ ingot having a diameter of 6 inches, a charge of 45 kg and a length of 80 mm is used and a border line of each region (void region, R-OSF region, $P_v$ region and $P_i$ region) existing in the CZ ingot as shown in FIG. 6 is specified by using a Cu decoration method, and thereafter samples (Y-1 and Y-6~Y-10) having a size of 4 mm×4 mm×7 mm are cut out from the ingot at 6 places shown in FIG. 6 and a transducer having a thickness of 10 μm and a C-axis inclined at an angle of 40° with respect to the surface of the sample and made of ZnO is directly provided on both surfaces of each of the samples. Then, the each sample is set in a quantitative evaluation device shown in FIGS. 1 and 2 to measure a change of elastic constant to a cooling temperature ($\Delta C_{44}/C_{44}$) when being cooled to 30 K-20 mK according to the quantitative evaluation method of the invention. The measured results are shown in FIG. 7. Moreover, an ordinate of FIG. 7 ($\Delta C_{44}/C_{44}$) is a relative value and shows that the values of the samples are shifted so as not to overlap with each other.

Comparative Example

A sample is prepared in the same manner as in the above example except that a transducer made of $LiNbO_3$ is attached to the surface of the sample Y-7 through an adhesive and the same measurement as in the example is conducted. The measured results are shown in FIG. 13.

In the measurement of the example, as seen from the results of FIG. 7, the samples Y-6~Y-8 of Pv region which has been considered to be rich in the frozen atomic vacancy region considerably lower the elastic constant in proportion to a reciprocal of a temperature within a cryogenic temperature region of 10 K-20 mK, whereas the change of elastic constant at the cryogenic temperature region is not recognized in the samples of the other region inclusive of $P_i$ region.

Figure 13:
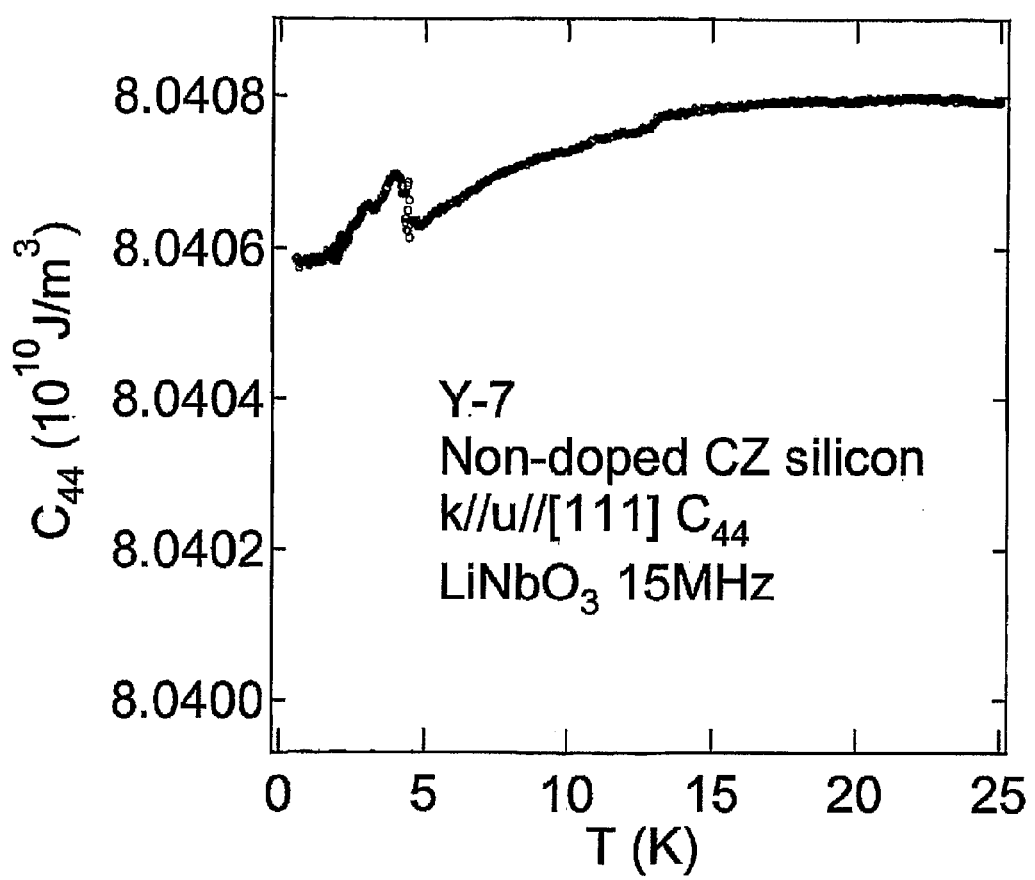
FIG. 13 is a graph showing results measured in a comparative example.

On the other hand, in the measurement of the comparative example, as seen from the results of FIG. 13, there is no change of elastic constant, which has been recognized in the example (Y-7) at the cryogenic temperature region of 10 K-20 mK. Moreover, the change of elastic constant can be confirmed at a temperature of about 4 K in FIG. 13, this change is due to the occurrence of poor adhesion (adhesion peeling) at the cryogenic temperature region. Therefore, it is considered that the accurate measurement can not be made by the occurrence of the poor adhesion.

Figure 12:
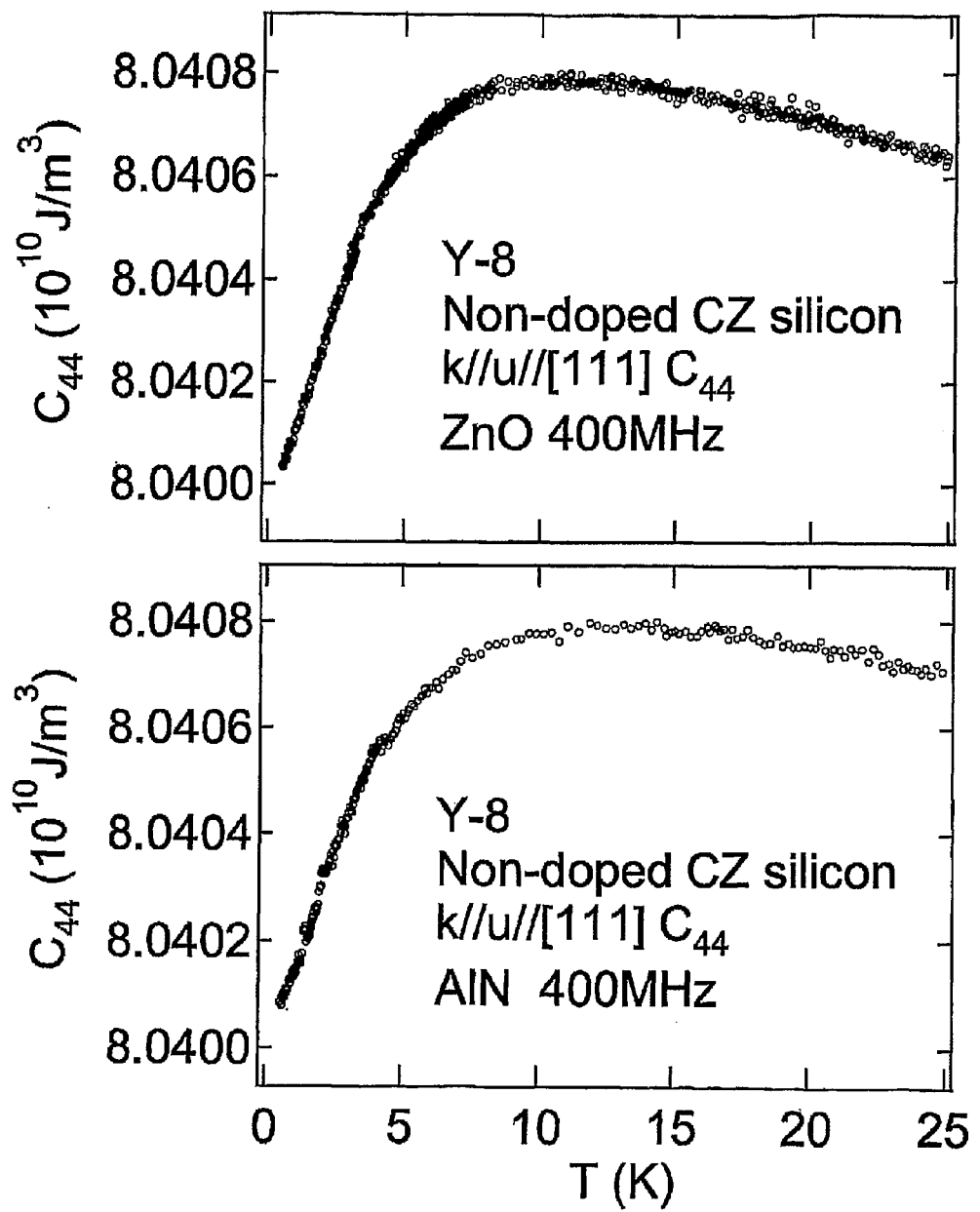
FIG. 12 is a graph showing a relation between elastic constant and temperature plotted in samples when a transducer is formed on each surface of two CZ silicon crystals cut out from the same sample, wherein an upper part shows results measured on a sample provided on its surface with ZnO as a transducer and a lower part shows results measured on a sample provided on its surface with AlN as a transducer.

Furthermore, an example plotting a relation between elastic constant and temperature in a sample provided on its surface with AlN as a transducer instead of ZnO is shown in a lower part of FIG. 12. Moreover, an upper part of FIG. 12 shows data plotting the relation between elastic constant and temperature in a sample obtained by forming ZnO as a transducer on a surface of the sample Y-8 used in FIG. 7 for the comparison. As seen from the results of FIG. 12, even when AlN is used as a transducer, there are obtained the results similar to those when ZnO is used as a transducer.

Figure 8:
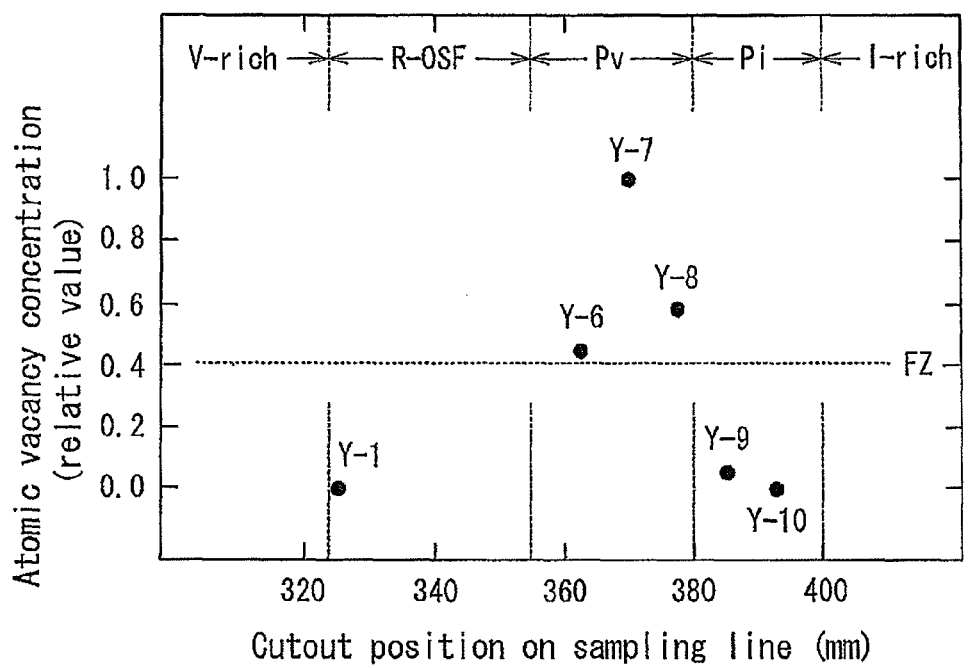
FIG. 8 is a graph showing results of atomic vacancy concentration calculated with respect to samples Y-1 and Y-6~Y-10 used in FIG. 7.

Then, results of atomic vacancy concentration calculated with respect to the samples Y-1 and Y-6~Y-10 are shown in FIG. 8. Moreover, the atomic vacancy concentration in an ordinate of FIG. 8 is represented by a relative value on the basis that the sample Y-7 is 1.0, provided that the actual atomic vacancy concentration of the sample Y-7 is $2.46 \times 10^{15}/cm^3$. The reduction of elastic constant is according to $C=C_0(T-T_C)/(T-\Theta)$. The difference $\Delta=T_C-\Theta$ between a characteristic temperature $T_C$ obtained in experiments and $\Theta$ is proportional to the atomic vacancy concentration N. The absolute value of the atomic vacancy concentration N can be empirically determined by a relational equation $N=\Delta \cdot C_0/\delta^2$ using $\Delta$ obtained in the experiment. Here, $\delta$ is a magnification of energy change in electron state of atomic vacancy to strain applied from exterior (deformation energy).

As seen from the results of FIG. 8, when the samples Y-6~Y-8 cut out from the $P_v$ region are compared with the samples Y-9 and Y-10 cut out from the $P_i$ region, the atomic vacancy concentration of the former samples is high, while the atomic vacancy concentration of the latter samples is low. Also, in the sample Y-1 cut out from the void region, the atomic vacancy is not existent and voids are existent, so that the atomic vacancy concentration becomes lower. Further, from the comparison among the samples Y-6~Y-8 cut out from the $P_v$ region, it is understood that the atomic vacancy concentration in the sample Y-7 cut out from a central position of the $P_v$ region is highest as compared with the atomic vacancy concentrations of the sample Y-6 positioned at a side of the R-OSF region and the sample Y-8 positioned at a side of the $P_i$ region.

INDUSTRIAL APPLICABILITY

According to the invention, the kind and existing concentration of atomic vacancy isolated in a wafer of silicon crystal produced by a Czochralski method (CZ method) or a floating zone method (FZ method) used in a semiconductor industry can be directly quantitatively evaluated by forming a rationalized thin-film transducer on a surface of a silicon sample without conducting an acceleration treatment for enhancing the concentration or the like.

Particularly, the demand of silicon wafer using a complete crystal with no secondary point defect such as voids or the like is rapidly increasing in the semiconductor industry. In the conventional technique, it is difficult to directly observe and quantitatively evaluate the concentration of atomic vacancy existing in the wafer, and hence there are problems such as a case that the reject rate of silicon device manufactured is high and the like. On the contrary, it is possible to quantitatively evaluate the kind and existing concentration of atomic vacancy by using the quantitative evaluation device of atomic vacancy according to the invention, which can be said to be vary large in the contribution to the semiconductor industry.

The invention claimed is:

1. A device for quantitatively evaluating atomic vacancy existing in a silicon wafer, which comprises:
    means for applying an external magnetic field to a silicon sample cut out from a given site of a silicon wafer,
    means for cooling the silicon sample to a temperature region of not higher than 50 K,
    means for oscillating an ultrasonic pulse to the surface of the silicon sample and propagating the oscillated ultrasonic pulse into the silicon sample and detecting a change of sound velocity in the propagated ultrasonic pulse,
    wherein a thin-film transducer having properties capable of following an expansion of the silicon sample associated with a temperature drop at the above temperature region and substantially aligning C-axis in a given direction is directly formed on the surface of the silicon sample;
    wherein the thin-film transducer has a C-axis inclined at an angle of 5-60° with respect to the surface of the silicon sample, and measures at least a transverse wave component among a vertical wave component and a transverse wave component propagated and detected in the silicon sample.

2. A device for quantitatively evaluating atomic vacancy existing in a silicon wafer according to claim 1, wherein the means for oscillating comprises means for detecting a phase difference between a reference wave pulse signal directly measured on the oscillated ultrasonic pulse and a sample passing wave pulse signal measured after the ultrasonic pulse is propagated into the silicon sample.

3. A device for quantitatively evaluating atomic vacancy existing in a silicon wafer according to claim 1, wherein the thin-film transducer is made from zinc oxide (ZnO) or aluminum nitride (AlN).

4. A device for quantitatively evaluating atomic vacancy existing in a silicon wafer according to claim 1 wherein the thin-film transducer is formed on the silicon wafer through a physical deposition method.

5. A device for quantitatively evaluating atomic vacancy existing in a silicon wafer according to claim 1, wherein a gold thin film is provided between the thin-film transducer and the silicon crystal.

6. A device for quantitatively evaluating atomic vacancy existing in a silicon wafer according to claim 1, wherein the thin-film transducer has a thickness of 0.5-200 μm.

7. A device for quantitatively evaluating atomic vacancy existing in a silicon wafer according to claim 1, wherein the thin-film transducer has a resonance frequency of 10 MHz-10 GHz.

8. A device for quantitatively evaluating atomic vacancy existing in a silicon wafer according to claim 1, wherein the means for applying applies the external magnetic field in a range of 0-20 tesla.

9. A device for quantitatively evaluating atomic vacancy existing in a silicon wafer according to claim 1, wherein the means for cooling further comprises a dilution refrigerator capable of cooling up to a cryogenic temperature of 5 mK.

10. A device for quantitatively evaluating atomic vacancy existing in a silicon wafer according to claim 1, wherein the ultrasonic pulse comprises a pulse width of not less than 10 μs.

11. A device for quantitatively evaluating atomic vacancy existing in a silicon wafer according to claim 1, wherein the means for oscillating further comprises a means for varying an oscillation frequency so as to render a phase difference produced by changing a sound velocity at a temperature or a magnetic field to conduct zero detection.

12. A device for quantitatively evaluating atomic vacancy existing in a silicon wafer according to claim 1, which is capable of simultaneously measuring phase difference at a plurality of silicon samples or at plural points of a single silicon sample to be measured.

13. A method for quantitatively evaluating atomic vacancy existing in a silicon wafer, which comprises:
  oscillating an ultrasonic pulse onto a silicon sample cut out from a given site of a silicon wafer and directly provided on its surface with a thin-film transducer having properties capable of following an expansion associated with a temperature drop of the silicon sample at a temperature region of not higher than 25 K at a state of applying an exterior magnetic field, if necessary, while cooling at the temperature region;
  propagating the oscillated ultrasonic pulse into the silicon sample;
  detecting a change of sonic velocity in the propagated ultrasonic pulse;
  calculating a reducing quantity of an elastic constant associated with the drop of the cooling temperature from the change of sonic velocity; and
  quantitatively evaluating a kind and a concentration of an atomic vacancy existing in the silicon wafer from the calculated reducing quantity of elastic constant;
  wherein the thin-film transducer has a C-axis inclined at an angle of 5-60° with respect to the surface of the silicon sample, and measures at least a transverse wave component among a vertical wave component and a transverse wave component propagated and detected in the silicon sample.

14. A device for quantitatively evaluating atomic vacancy existing in a silicon wafer according to claim 2, wherein the thin-film transducer is formed on the silicon wafer through a physical deposition method.

15. A device for quantitatively evaluating atomic vacancy existing in a silicon wafer according to claim 3, wherein the thin-film transducer is formed on the silicon wafer through a physical deposition method.

16. A device for quantitatively evaluating atomic vacancy existing in a silicon wafer according to claim 2, wherein a gold thin film is provided between the thin-film transducer and the silicon crystal.

17. A device for quantitatively evaluating atomic vacancy existing in a silicon wafer according to claim 3, wherein a gold thin film is provided between the thin-film transducer and the silicon crystal.

18. A device for quantitatively evaluating atomic vacancy existing in a silicon wafer according to claim 4, wherein a gold thin film is provided between the thin-film transducer and the silicon crystal.

19. A device for quantitatively evaluating atomic vacancy existing in a silicon wafer, which comprises:
  a magnetic force generator applying an external magnetic field to a silicon sample cut out from a given site of a silicon wafer,
  a temperature controller cooling the silicon sample to a temperature region of not higher than 50 K,
  an ultrasonic oscillator oscillating an ultrasonic pulse to the surface of the silicon sample and propagating the oscillated ultrasonic pulse into the silicon sample and detecting a change of sound velocity in the propagated ultrasonic pulse, wherein a thin-film transducer having properties capable of following an expansion of the silicon sample associated with a temperature drop at the above temperature region and substantially aligning C-axis in a given direction is directly formed on the surface of the silicon sample;
  wherein the thin-film transducer has a C-axis inclined at an angle of 5-60° with respect to the surface of the silicon sample, and measures at least a transverse wave component among a vertical wave component and a transverse wave component propagated and detected in the silicon sample.

\* \* \* \* \*